United States Patent [19]
Malmström

[11] Patent Number: 5,835,557
[45] Date of Patent: Nov. 10, 1998

[54] APPARATUS FOR DISPLAYING X-RAY IMAGES

[75] Inventor: Kent Malmström, Rimforsa, Sweden

[73] Assignee: Swemac Orthopaedics AB, Linkoping, Sweden

[21] Appl. No.: 809,645
[22] PCT Filed: Oct. 11, 1995
[86] PCT No.: PCT/SE95/01167
§ 371 Date: Mar. 26, 1997
§ 102(e) Date: Mar. 26, 1997
[87] PCT Pub. No.: WO96/11633
PCT Pub. Date: Apr. 25, 1996

[30] Foreign Application Priority Data

Oct. 13, 1994 [SE] Sweden .................................. 9403497

[51] Int. Cl.$^6$ ........................................................ A61B 6/00
[52] U.S. Cl. ............................................ 378/197; 378/193
[58] Field of Search .................................. 378/193, 195, 378/196, 197, 198

[56] References Cited

U.S. PATENT DOCUMENTS

| | | | |
|---|---|---|---|
| 4,150,297 | 4/1979 | Borggren ........................... | 378/197 X |
| 4,209,706 | 6/1980 | Nunan ................................ | 378/197 X |
| 4,961,214 | 10/1990 | Van Endschot et al. ............... | 378/197 |
| 5,038,371 | 8/1991 | Janssen et al. .......................... | 378/197 |
| 5,095,501 | 3/1992 | Kobayashi . | |
| 5,367,554 | 11/1994 | Kobayashi et al. . | |
| 5,386,453 | 1/1995 | Harrawood et al. . | |
| 5,515,416 | 5/1996 | Diczek et al. .......................... | 378/197 |

*Primary Examiner*—David P. Porta
*Attorney, Agent, or Firm*—Sixbey, Friedman, Leedom & Ferguson; Frank P. Presta; Joseph S. Presta

[57] ABSTRACT

An apparatus comprising a first X-ray image system and a second X-ray image system. Each X-ray image system includes a devices for emitting X-rays and a radiation receiving device located in the direction of the radiation. These are disposed, on receiving radiation, to emit signals to a TV-monitor. The two X-ray image systems form an integral X-ray image unit which is supported by a carrier device. By means of a connection device, the X-ray image unit is movably connected to the carrier device and, in association with the connection device, the X-ray image unit is movably journalled for altering the angle of inclination of a plane through the center axes of the rays for the two X-ray image systems.

8 Claims, 4 Drawing Sheets

APPARATUS FOR DISPLAYING X-RAY IMAGES

The present invention relates to an apparatus comprising a first X-ray image system and a second X-ray image system forming an X-ray image unit.

In the employment of apparatuses of the above type for, for example, fluoroscopy of a patient, there is a need to be able to adapt the adjustment position of the apparatus after changes in the orientation of those organs in the process of being exposed to fluoroscopy. In, for example, a spinal examination, attempts are made to orient the plane of fluoroscopy at a right angle to the spine. Since the spine curves particularly at the lower lumbar region, it is necessary that the corresponding adaptation can be made to the orientation of the plane of fluoroscopy. Also in the examination of and surgical intervention in the region of the neck of the femur, there is a corresponding need to be able readily to alter the orientation of the plane of fluoroscopy.

There are also needs in many contexts for a mobile apparatus for, for example, fluoroscopy, in which the apparatus is disposed to be placed so as to surround a bed with the patient recumbent in the bed.

The present invention relates to an apparatus in which the above-indicated needs are satisfied. This is put into effect by means of the technique.

In one embodiment, at least one of the interconnection devices of the apparatus includes at least one annular-like peripheral surface which co-operates with a journal in which the interconnection device is displaceable in relation to the carrier means of the apparatus in a circumferential direction of the annular peripheral surface. Hereby, the X-ray image unit, and thereby the X-ray image systems will be rotated in the plane which is formed through the centre axes of the rays.

In a further embodiment, each respective interconnection device is journalled in a path along which the interconnection device is displaceable, this path having substantially vertical orientation.

This arrangement compensates for the displacement in the lateral direction on alteration of the inclination of the plane which passes through the centre axes of the rays.

Further expedient embodiments of the present invention are also dis- closed in the appended claims.

The present invention will now be described in greater detail hereinbelow, with reference to a number of drawing figures, in which.

Figure 1:
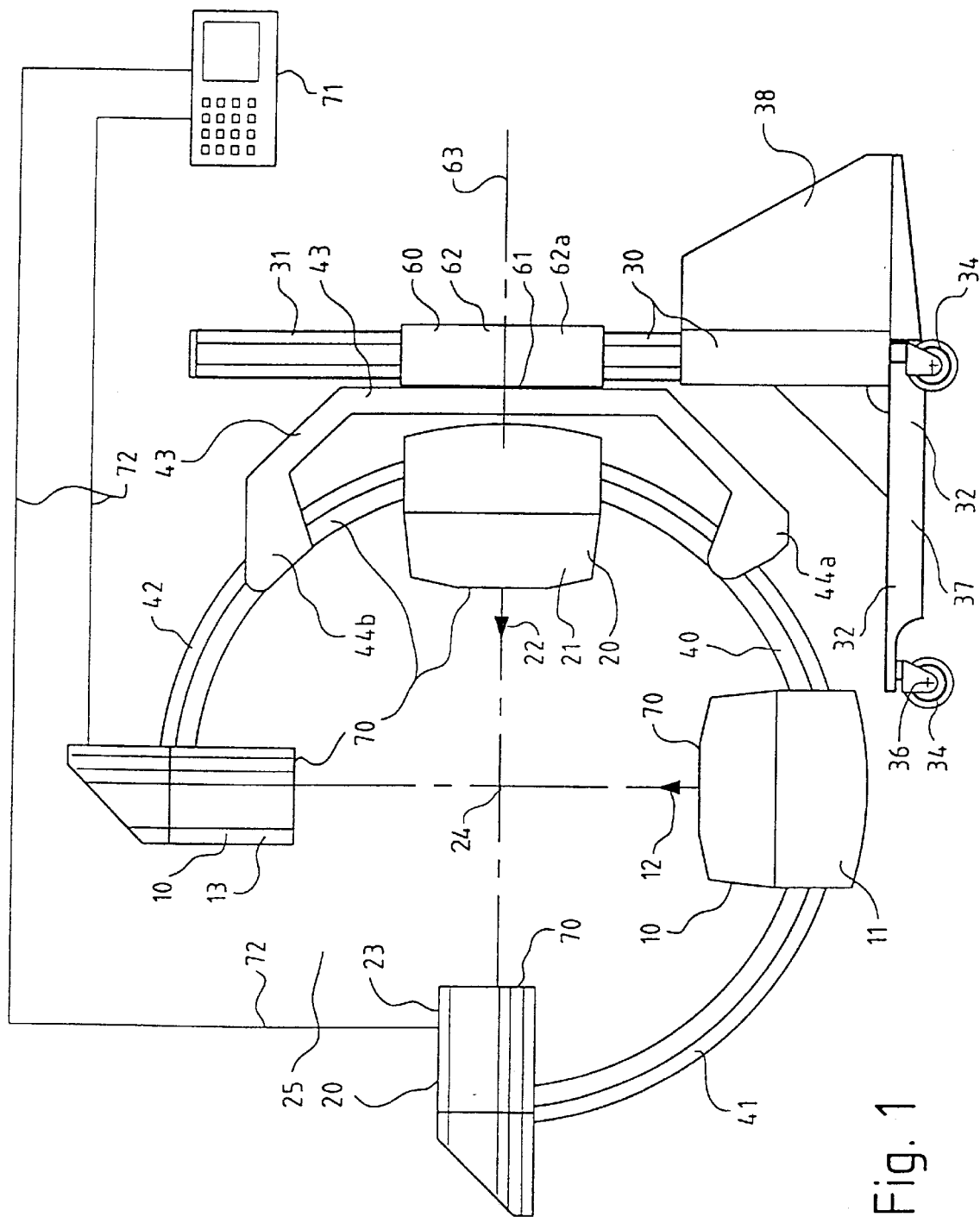
FIG. 1 is a side elevation of an apparatus according to the invention.
Figure 2:
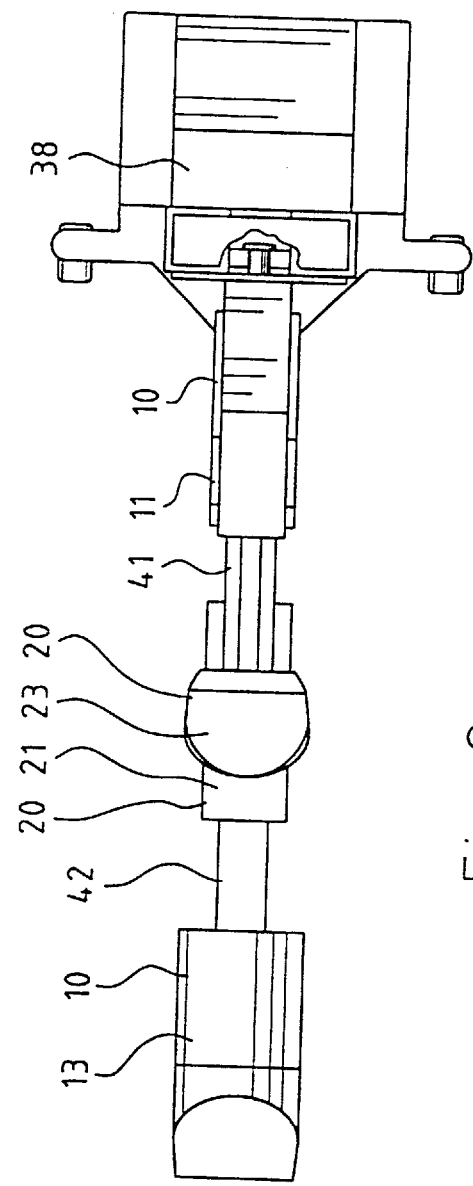
FIG. 2 shows the apparatus according to FIG. 1 seen from one edge.

FIGS. 1 and 2 show a first embodiment of an apparatus according to the invention. The apparatus includes a first X-ray image system 10 and a second X-ray image system 20 each one comprising two units 11,21 and 13,23, respectively. The one unit 11,21 forms a device 11,21 provided with X-ray tubes for emitting X-rays, and the other unit 13,23 forms a radiation receiving device 13,23 located in the direction 12,22 of the radiation. Each one of the two X-ray image systems 10,20 thus includes a device 11,21 for emitting X-rays and a device 13,23 for receiving X-rays.

Each respective radiation receiving device 13,23 is disposed, on received radiation, to emit signals which are electrically transmitted via leads 72 or in wireless mode via a transmitter (not shown) to a receiver unit 71, generally in the form of a TV-monitor 71. The signals are stored in the receiver unit and/or are reproduced as an image of an irradiated object which is located between those devices which emit the X-rays and those devices which receive them. The centre axes 12 of the radiation for the first X-ray image system is substantially at right angles to the centre axis 22 of the rays of the second X-ray image system 20. The point of intersection between the centre axes of the rays carries reference numeral 24.

Both of the X-ray image systems 10,20 are kept in mutually fixed positions by mechanical interconnection devices 40,41,42 and thereby form an integral X-ray image unit 70. The devices 11,12 for emitting X-rays and the devices 13,23 for receiving the X-rays are disposed on the interconnection devices 40–42 such that the X-rays are located in a plane through these devices 11,12; 21,23.

The interconnection devices 40–42 are placed such that the X-ray image unit 70 has no mechanical connection between two units 11,21 and 13,23, respectively, for emitting X-rays or for receiving such X-rays, in which event the one unit 11,21 is included in the first X-ray image system 10 and the second unit 13,23 is included in the second X-ray image system 20. Through the opening 25 which is formed between two units, accessibility is improved to the patient, for example to facilitate the surgeon's work or for altering the position of the patient. As a rule, the direction of the "free", area (the opening) 25 created as a result of the described arrangement of the X-ray image unit 70 is, seen from the point of intersection 24 of the centre axes 12,22 of the rays, an oblique upward direction, in other words the "free", area 25 encompasses a straight line departing from the point of intersection 24 which makes an angle with horizontal plane within a range of approx. 10°–80°, preferably approx. 20°–70°.

The X-ray image unit also includes a coupling device 43, hereinafter also designated arc 43 which, by means of a connection device 60, is connected to a carrier device 30. In the figures, the apparatus is shown in one embodiment in which the connection device 60 is, via a mechanical shaft 61, connected to the coupling device 43. The connection is designed such that the coupling device is rotary about the geometric centre axis 63 of the shaft 61. The connection device 60 also includes at least one retainer device 62, preferably a sleeve-like device 62 whose elongate central cavity is substantially vertical in orientation.

The coupling device 43 is, in the illustrated embodiment, designed as an arc 43 whose both end portions 44$a,b$ have passages which co-operate with two mutually adjacent interconnection devices 40,42 of which the one, 42 alone supports the highest-located unit 21 for emitting X-rays or the highest-located unit for receiving X-rays. In one embodiment, the passages are designed as grooves in which the interconnection devices 40,42 may be displaced in a circular path whose centre essentially coincides with that region in which the point of intersection 24 of the centre axes of the X-rays 12,22 is located. Those parts of the interconnection devices 40,42 which co-operate with the passages of the end portions 44,$a,b$ generally form parts of an arc of a circle.

The carrier device 30 includes a lower portion 32 which carries a substantially vertical column 31. This has a cross-section of good fit with the inner cross-section of the retainer device 62. This makes possible displacement of the retainer device and, thereby, of the arc 43 in a vertical direction while maintaining orientation of the arc in the horizontal direction.

Figure 3:
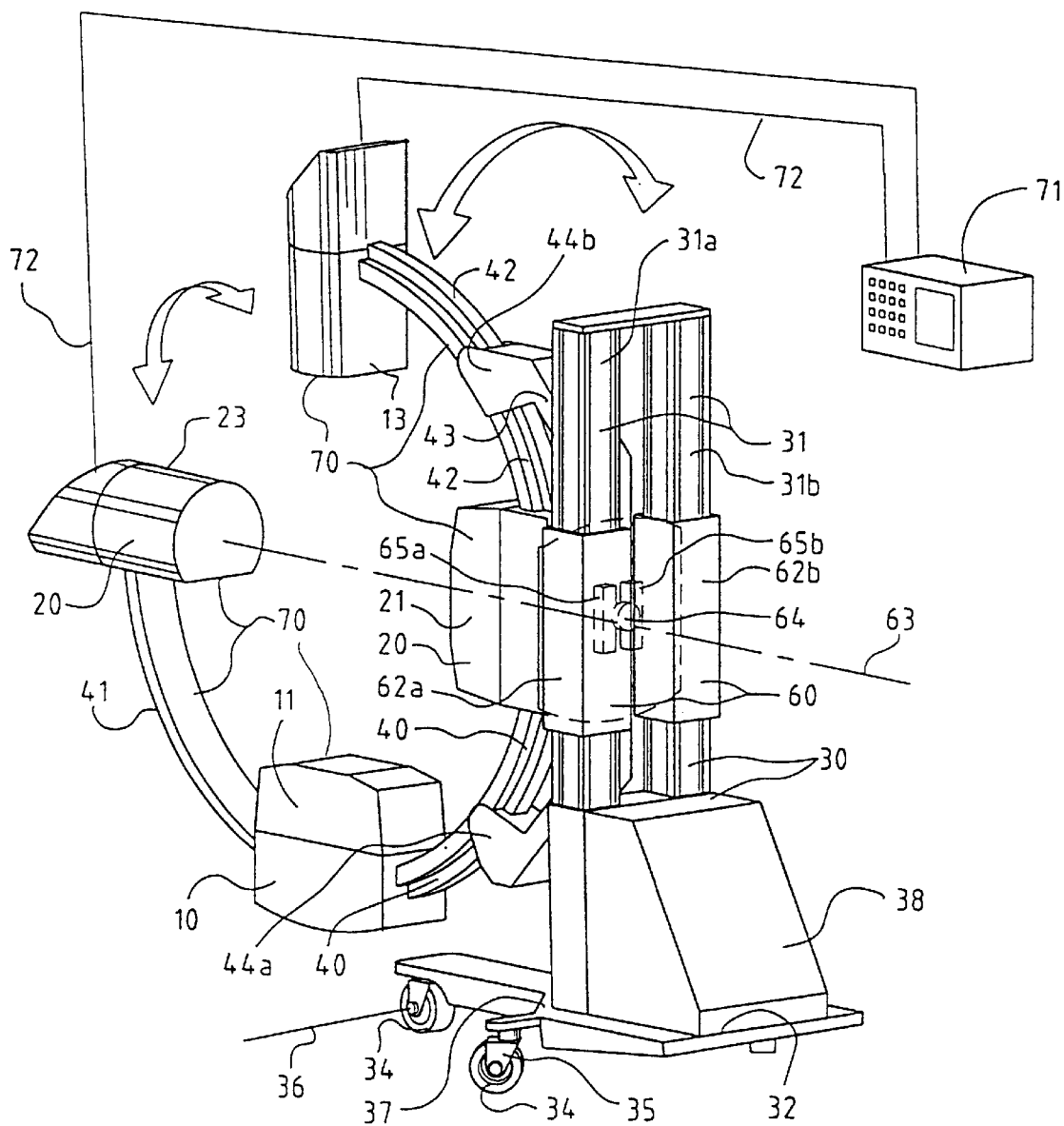
FIG. 3 is a perspective view of a second embodiment of the apparatus according to the invention.
Figure 4:
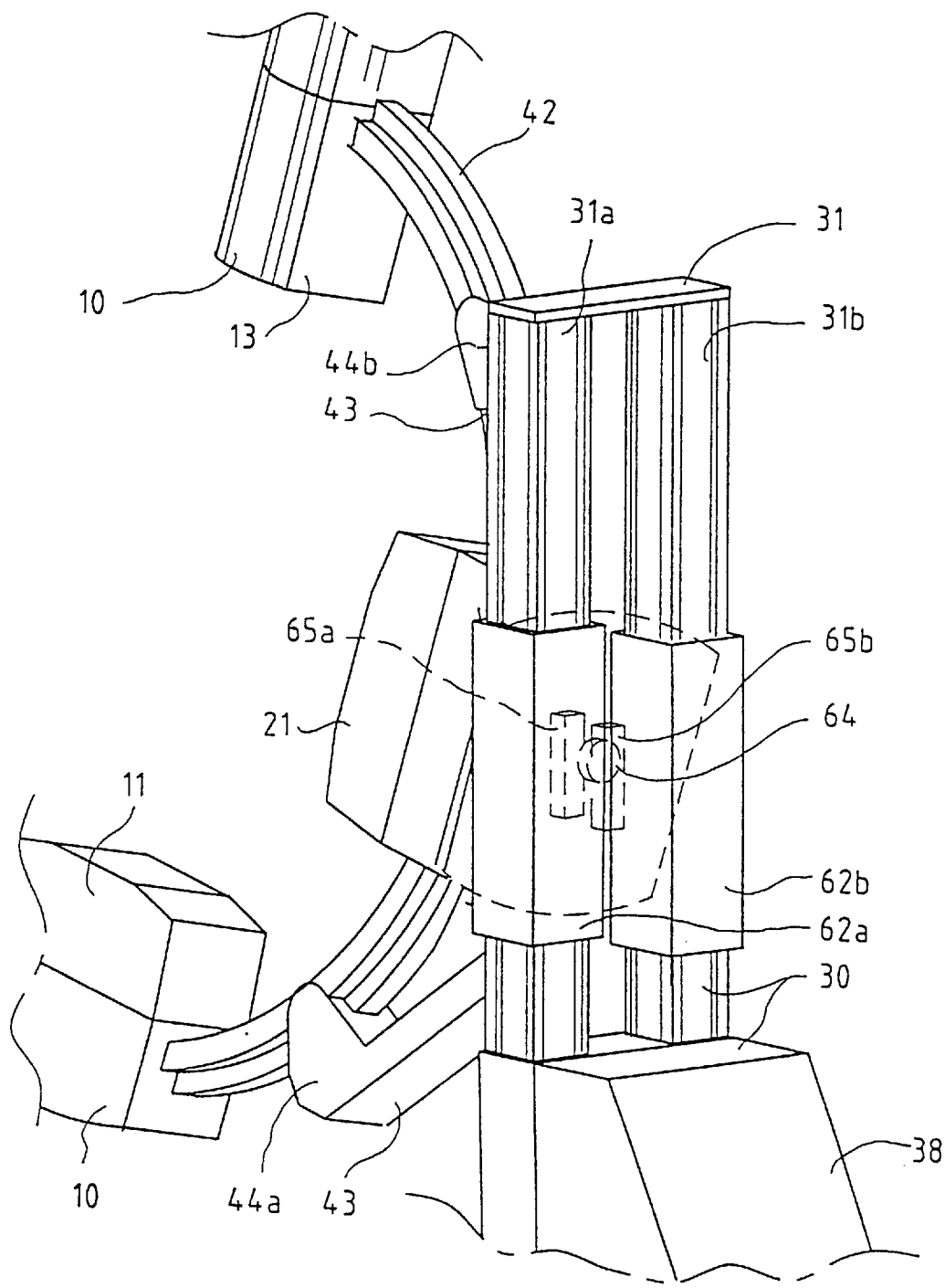
FIG. 4 is a view corresponding to that of FIG. 3 with the X-ray image unit of the apparatus in an angled position in relation to the vertical plane.

The above described design of the connection device 60 constitutes but one example of an embodiment of the apparatus. It will be obvious to a person skilled in the art that, in alternative embodiments, the vertical column 31 is designed with a part which is included in the column and is displaceable in the vertical direction, for example a telescopic part which is located under the coupling device (the arc) 43 located between the connection device 60 and the carrier device 30 or which supports the connection device 60. FIGS. 3 and 4 show one embodiment of the apparatus in which the vertical column 31 is composed of two column parts 31a,31b. The retainer device 62 is also composed of two retainer device parts 62a,b. Both the column parts and the retainer parts are of a design which corresponds to that described in connection with FIGS. 1 and 2 for the column 31 and the retainer device 62. The parts are disposed to be displaced synchronously with one another either by displacement devices (not shown) or manually. In one embodiment, they are also disconnected or disconnectable from one another in order to make possible individual displacement (cf. FIG. 4). A drive means 64 is fixed to the coupling device 43 via one or more connection devices 60 and is rotary in relation to the column 31 about a geometric axis 63 (FIGS. 3 and 4) with a placing corresponding to that previously described for the geometric axes 63 of the mechanical shaft 61. Driver arms 65a,b are provided to operate in response to relative movement between the retainer parts 62,a,b and when necessary rotate the drive means 64 and thereby the X-ray image unit to a position angled in relation to vertical plane (cf. FIG. 4).

As a rule, both the devices 11,21 for emitting X-rays and the devices 13,23 for receiving X-rays are displaceable in a direction towards one another for setting their mutual spacing. In that the devices are individually displaceable and the X-ray image unit 70 rotary in the end portions 44a,b of the arc 43, the effect will be achieved that, while maintaining both the patient's and the apparatus's positions, the point of intersection of the centre axis of the rays may be set to that position which is occasioned by pertinent requirements. In the embodiment illustrated in the figures, the lower portion 32 of the carrier device 30 includes a frame 37 which is carried by two opposing wheel panics. The axis of rotation for each respective wheel 34 carries reference numeral 36. For connecting the wheels 34 to the lower portion 32, the lower portion is generally provided with wheel forks 35 in which the wheels 34 are journalled.

In turn, the wheel forks are rotatably journalled in the lower portion 32. This journalling is effected such that at least one wheel 34 in each wheel pair is lockable. At least for two of the locked wheels, the wheel axes make substantially right angles with one another. Preferably, the one wheel is locked in a position in which the wheel has an orientation entailing that its axis of rotation 36 is parallel with a plane through the centre axes 12,22 of the rays, and the second wheel is of an orientation which entails that the axis of rotation 36 of the wheel has a direction at right angles to the above-mentioned direction.

In order to constitute a counterweight to the X-ray image unit 70, a weight 38 is provided in connection with the lower portion 32 of the carrier device. In this instance, the weight is placed in relation to the X-ray image unit on the opposite side of the wheel pair disposed most distally from the X-ray image unit. This implies that the weight 38 balances the X-ray image unit utilizing of a fulcrum.

In the foregoing, it has generally been disclosed that mechanical interconnection devices 40–42 co-operate with end portions 44a,b in order to permit the interconnection devices to describe an annular-like movement about the intersection point 24 of the centre axes of the rays 12,22. In order to realize this, the interconnection devices are, in one embodiment in which they abut against the end portions 44,a,b , designed with annular-like peripheral surfaces which abut against journals disposed in the end portions.

When the apparatus is put into use, it is placed such that a lower X-ray emitting or X-ray receiving device 11,13 in the substantially vertically disposed X-ray image system is located beneath the patient who is to be treated. The patient will thereby be located in the space between the devices 11,21 (provided with X-ray tubes) and the X-ray receiving devices 13,23 of the two X-ray image systems. By relative displacement of the part of the body and the apparatus, a continuous fluoroscopy of the part of the body takes place. The results are displayed on the screen of the TV-receiver. When, in fluoroscopy, the operator finds that the inclination of the plane which is formed by the X-rays needs to be corrected, the inclination of the plane through the centre axes of the rays is altered and/or the X-ray image unit 70 is rotated in the circumferential direction. If necessary, the X-ray image systems 10,20 are displaced upwards or downwards by movement of the connection device 60 along the vertical column 31 of the carrier device 30. Requisite adjustment of the positions of the X-ray emitters and X-ray receivers also takes place.

The connections/journals disclosed in the body of the description in which displacements of the interconnection devices 40,42 and retainer device 62 of the connection devices 60 takes place are, in the simplest case, in the form of sliding couplings, but it is obvious that this construction is adapted to meet the specific needs for which the apparatus according to the invention is dimensioned. Thus, for example, in certain embodiments roller bearings are provided. Driving of these movements also varies from purely manual action to motor-driven displacements. Hydraulic power for such displacement is also employed. The above detailed description has referred to but a limited number of embodiments of the present invention, but a person skilled in the art will readily perceive that the present invention encompasses a large number of embodiments without departing from the spirit and scope of the appended claims.

I claim:

1. An apparatus comprising a first X-ray image system and a second X-ray image system, in which each X-ray image system includes a device provided with X-ray tubes for emitting X-rays, and an X-ray receiving device located in the direction of the rays and disposed, on receiving radiation, to emit signals for transfer to a receiver for storage in the monitor and/or reproduction as an image of an irradiated object which is located between said devices emitting X-rays and said devices receiving such X-rays, in which the radiation direction of the first X-ray image system is substantially at right angles to the radiation direction of the second X-ray image system, in which both of the X-ray image systems are held in mutually fixed positions by mechanical interconnection devices for forming an X-ray image unit, and in which the X-ray image unit is supported by a carrier device, characterized in that the X-ray image unit is, by means of a connection device, movably connected to the carrier device; and that the X-ray image unit is, in association with said connection device, movably journalled for altering the angle of inclination of the plane through the centre axes of the rays for both of the X-ray image systems, wherein the carrier device includes a substantially vertical column for co-operation with the connection device, and that said column includes at least one portion of a cross-section which is of good fit with the inner cross-section of at least one retainer device disposed on the connection device, so as to make possible vertical displacement of the connection device in relation to the carrier device, the vertical column including two column parts disposed parallel with one another.

2. The device as claimed in claim 1, characterized in that the X-ray image unit is rotary in relation to the carrier device about a substantially horizontal geometric axis.

3. The apparatus as claimed in claim 2, characterized in that the geometric axis also constitutes a geometric centre axis for a mechanical shaft into interconnecting the X-ray image unit with the connection device.

4. The apparatus as claimed in claim 1, characterized in that the X-ray image systems of the X-ray image unit include interconnection devices fixing the devices of the X-ray image systems provided with X-ray tubes and the radiation receiving devices of the X-ray image systems in mutually fixed positions.

5. The apparatus as claimed in claim 1, characterized in that the X-ray image unit is connected to the connection device via a coupling device with two mutually spaced apart end portions for fixing the X-ray image unit .

6. The apparatus as claimed in claim 1, characterized in that the X-ray image unit includes a portion which has no direct mechanical connection between two units comprising devices provided with X-ray tubes or radiation receiving devices; that said portion is directed obliquely upwards from the point of intersection of the center axes of the rays; and/or that end portions of the coupling device co-operate with two mutually adjacent interconnecting devices of which the one alone supports the highest-located unit for emitting X-rays or the highest-located unit for receiving X-rays.

7. The device as claimed in claim 6, characterized in that the interconnection devices with which the end portions of the coupling device co-operate for fixing the X-ray image unit are disposed to be displaced in relation to the end portions along a part of an arc of a circle with the center in the point of intersection of the centre axes of the radiation.

8. The apparatus as claimed in claim 1, characterized in that the carrier device of the apparatus is provided with wheels so as to make possible movement of the apparatus in relation to that object which is to be irradiated; and that at least two of said wheels are lockable for temporary fixation of the carrier device and thereby the apparatus in a position set in relation to the pertinent irradiation object.

* * * * *